US012570762B2

(12) United States Patent
Li

(10) Patent No.: US 12,570,762 B2
(45) Date of Patent: Mar. 10, 2026

(54) CONJUGATE OR FUSION PROTEIN FOR CANCER THERAPY

(71) Applicant: Beijing Neoletix Biological Technology Co., Ltd., Beijing (CN)

(72) Inventor: Qi Li, Lawrenceville, GA (US)

(73) Assignee: Beijing Neoletix Biological Technology Co., Ltd., Beijing (CN)

( * ) Notice: Subject to any disclaimer, the term of this patent is extended or adjusted under 35 U.S.C. 154(b) by 627 days.

(21) Appl. No.: 17/930,370

(22) Filed: Sep. 7, 2022

(65) Prior Publication Data

US 2024/0076401 A1     Mar. 7, 2024

(51) Int. Cl.
| | |
|---|---|
| *C07K 16/30* | (2006.01) |
| *A61K 47/64* | (2017.01) |
| *A61K 47/65* | (2017.01) |
| *A61K 47/68* | (2017.01) |
| *A61P 35/00* | (2006.01) |
| *C07K 16/28* | (2006.01) |

(52) U.S. Cl.
CPC .......... *C07K 16/3007* (2013.01); *A61K 47/64* (2017.08); *A61K 47/65* (2017.08); *A61K 47/68031* (2023.08); *A61P 35/00* (2018.01); *C07K 16/2803* (2013.01); *C07K 2317/32* (2013.01)

(58) Field of Classification Search
CPC ............ C07K 16/3007; C07K 2317/32; C07K 2317/22; C07K 2317/569; C07K 2319/74; C07K 16/2803; C07K 2317/51; C07K 2317/565; C07K 2319/00; A61K 47/64; A61K 47/65; A61K 47/68031; A61K 38/191; A61K 38/2013; A61K 47/642; A61K 2039/505; A61K 47/6849; A61K 47/6851; A61K 47/6889; A61P 35/00
See application file for complete search history.

(56) References Cited

FOREIGN PATENT DOCUMENTS

| | | | |
|---|---|---|---|
| WO | 2019241847 A1 | 12/2019 | |
| WO | WO-2020226907 A1 * | 11/2020 | ................ A61P 7/00 |

OTHER PUBLICATIONS

Rudikoff et al. Proceedings of the National Academy of Sciences USA, vol. 79, p. 1979-1983, 1982 (Year: 1982).*
Gillies. Proc. Nati. Acad. Sci. USAvol. 89, pp. 1428-1432, 1992 (Year: 1992).*
Bendig. Methods: Companion to Methods in Enzymology 9, 893, 1995 (Year: 1995).*
Johnson and Wu. Methods in Molecular Biology, Antibody Engineering: Methods and Protocols, vol. 248, p. 11-25, 2004 (Year: 2004).*
Dubel. Handbook of Therapeutic Antibodies, 2007, p. 100-101 (Year: 2007).*
Drabek et al. Front Immunol. Dec. 19, 2016;7:619, 1-10 (Year: 2016).*
Smith et al. Blood Adv. 2018;2(16)_2072-2078 (Year: 2018).*
Yap et al. Theranostics. Feb. 7, 2019;9(4):1154-1169 (Year: 2019).*
Abdel-Latif et al. World J Clin Oncol Jul. 24, 2020; 11(7): 464-476 (Year: 2020).*
Yin. The Medicine Maker (Jul. 24, 2020). Driving Antibody Drug Discovery Through GenScript ProBio (Year: 2020).*
Yap, May Lin, et al. "Activated platelets in the tumor microenvironment for targeting of antibody-drug conjugates to tumors and metastases" Theranostics Feb. 2019, vol. 9, Issue 4, pp. 1154-1169.

* cited by examiner

*Primary Examiner* — Sean E Aeder
*Assistant Examiner* — Yie Chia Lee
(74) *Attorney, Agent, or Firm* — Perkins Coie LLP; Viola Kung

(57) ABSTRACT

The present invention relates to a conjugate or a fusion protein comprising: (a) an anti-TLT-1 (triggering receptors expressed on myeloid cells like transcript-1) antibody, and (b) a payload, wherein the anti-TLT-1 antibody and the payload are covalently linked together, and the payload is an anti-neoplastic molecule, an anti-mitotic molecule, a transcription or translation inhibitor, or a cytokine. The anti-TLT-1 antibody directs and targets the conjugate or the fusion protein to activated platelets in a tumor microenvironment (TME) through binding of the antibody to TLT-1, a membrane protein receptor that is only present on activated platelets. As a result, the targeted cytotoxic molecules or therapeutic proteins effectively inhibit the tumor growth. The present invention also relates to specific single domain antibodies (sdAbs) or sdAb based heavy chain-only antibody (HcAb) against TREM (triggering receptors expressed on myeloid cells) like transcript-1 (TLT-1).

7 Claims, 9 Drawing Sheets

Specification includes a Sequence Listing.

| Clone ID | CDR1 (SEQ ID NO) | CDR2 (SEQ ID NO) | CDR3 (SEQ ID NO) |
|---|---|---|---|
| AHP11901 | GFDSAYYV (1) | IGTSSGTT (2) | ALANRWYPTLARHDYLF (3) |
| AHP11903 | GSIFSINA (4) | LTTSGTQ (5) | YVQGQNVLGGILRDY (6) |
| AHP11924 | GSIFSINA (7) | LTTSGTQ (8) | YVQGQSVLGGILRDY (9) |
| AHP11939 | GSDFSLAH (10) | ITSHGRT (11) | YIQWSDSTT (12) |
| AHP11946 | GSIFSINA (13) | LTTGGTT (14) | YVQGQQYLGDSLRDY (15) |
| AHP11983 | GFTFSDYN (16) | ITQTGAAT (17) | RRGWPVLGDRDDY (18) |
| AHP11986 | ASGRTTYT (19) | IIPTGGTI (20) | ALKISGPVTTLQEDYDY (21) |
| AHP11989 | GSTVIDYA (22) | IDSNGRRT (23) | AAGNRGPRDDIGQYYY (24) |
| AHP11993 | ESTLDNYA (25) | ITKGGSFV (26) | AAKRSYYVCSPDDYDY (27) |
| AHP11995 | GPTGFITG (28) | LFNSGTT (29) | NIRMYDSRRYSD (30) |
| AHP11997 | GIAFSIYA (31) | ITSGAST (32) | NAKFLGLDY (33) |
| AHP12001 | ASGRTTYT (34) | ISPTGGTI (35) | ALKISGPVTTLEEDYDY (36) |
| AHP12006 | GFDSAYYV (37) | IGTSSGTT (38) | ALANRWYPTLVRHDYLF (39) |
| AHP12018 | GFTSSNYR (40) | RTGAGGAT (41) | YYCNAFDSENQNNY (42) |
| AHP12019 | AFTSSNYR (43) | RTGAGGAT (44) | YYCNAIDFENQNNY (45) |
| AHP12022 | GFTASNYR (46) | RNGPGGRT (47) | YYCNAIDMGNSNAY (48) |
| AHP12024 | AFTSSNYR (49) | RTGAGGAT (50) | YYCNAIDFENQSNY (51) |
| AHP12026 | AFTSSNYR (52) | RTGAGGAT (53) | YYCNAIDFENQTNY (54) |
| AHP12028 | GFTSNNYR (55) | RTGAGGAT (56) | YYCNAFDSENQSNY (57) |
| AHP12034 | GLTFSDYD (58) | KASADGRT (59) | NARRNWGGRPQDY (60) |

FIG. 1B mc-vc-PAM-MMAE: Maleimido-caproyl-valine-citrulline-para-aminobenzyl-MMAE

SEQUENCE LISTING

```
Sequence total quantity: 61
SEQ ID NO: 1          moltype = AA  length = 8
FEATURE               Location/Qualifiers
source                1..8
                      mol_type = protein
                      organism = Lama glama
SEQUENCE: 1
GFDSAYYV                                              8

SEQ ID NO: 2          moltype = AA  length = 8
FEATURE               Location/Qualifiers
source                1..8
                      mol_type = protein
                      organism = Lama glama
SEQUENCE: 2
IGTSSGTT                                              8
```

-continued

```
SEQ ID NO: 3          moltype = AA   length = 17
FEATURE               Location/Qualifiers
source                1..17
                      mol_type = protein
                      organism = Lama glama
SEQUENCE: 3
ALANRWYPTL ARHDYLF                                               17

SEQ ID NO: 4          moltype = AA   length = 8
FEATURE               Location/Qualifiers
source                1..8
                      mol_type = protein
                      organism = Lama glama
SEQUENCE: 4
GSIFSINA                                                          8

SEQ ID NO: 5          moltype = AA   length = 7
FEATURE               Location/Qualifiers
source                1..7
                      mol_type = protein
                      organism = Lama glama
SEQUENCE: 5
LTTSGTQ                                                           7

SEQ ID NO: 6          moltype = AA   length = 15
FEATURE               Location/Qualifiers
source                1..15
                      mol_type = protein
                      organism = Lama glama
SEQUENCE: 6
YVQGQNVLGG ILRDY                                                 15

SEQ ID NO: 7          moltype = AA   length = 8
FEATURE               Location/Qualifiers
source                1..8
                      mol_type = protein
                      organism = Lama glama
SEQUENCE: 7
GSIFSINA                                                          8

SEQ ID NO: 8          moltype = AA   length = 7
FEATURE               Location/Qualifiers
source                1..7
                      mol_type = protein
                      organism = Lama glama
SEQUENCE: 8
LTTSGTQ                                                           7

SEQ ID NO: 9          moltype = AA   length = 15
FEATURE               Location/Qualifiers
source                1..15
                      mol_type = protein
                      organism = Lama glama
SEQUENCE: 9
YVQGQSVLGG ILRDY                                                 15

SEQ ID NO: 10         moltype = AA   length = 8
FEATURE               Location/Qualifiers
source                1..8
                      mol_type = protein
                      organism = Lama glama
SEQUENCE: 10
GSDFSLAH                                                          8

SEQ ID NO: 11         moltype = AA   length = 7
FEATURE               Location/Qualifiers
source                1..7
                      mol_type = protein
                      organism = Lama glama
SEQUENCE: 11
ITSHGRT                                                           7

SEQ ID NO: 12         moltype = AA   length = 9
FEATURE               Location/Qualifiers
source                1..9
                      mol_type = protein
                      organism = Lama glama
SEQUENCE: 12
YIQWSDSTT                                                         9
```

-continued

```
SEQ ID NO: 13           moltype = AA  length = 8
FEATURE                 Location/Qualifiers
source                  1..8
                        mol_type = protein
                        organism = Lama glama SEQUENCE: 13
GSIFSINA                                                                 8

SEQ ID NO: 14           moltype = AA  length = 7
FEATURE                 Location/Qualifiers
source                  1..7
                        mol_type = protein
                        organism = Lama glama SEQUENCE: 14
LTTGGTT                                                                  7

SEQ ID NO: 15           moltype = AA  length = 15
FEATURE                 Location/Qualifiers
source                  1..15
                        mol_type = protein
                        organism = Lama glama SEQUENCE: 15
YVQGQQYLGD SLRDY                                                         15

SEQ ID NO: 16           moltype = AA  length = 8
FEATURE                 Location/Qualifiers
source                  1..8
                        mol_type = protein
                        organism = Lama glama SEQUENCE: 16
GFTFSDYN                                                                 8

SEQ ID NO: 17           moltype = AA  length = 8
FEATURE                 Location/Qualifiers
source                  1..8
                        mol_type = protein
                        organism = Lama glama SEQUENCE: 17
ITQTGAAT                                                                 8

SEQ ID NO: 18           moltype = AA  length = 13
FEATURE                 Location/Qualifiers
source                  1..13
                        mol_type = protein
                        organism = Lama glama SEQUENCE: 18
RRGWPVLGDR DDY                                                           13

SEQ ID NO: 19           moltype = AA  length = 8
FEATURE                 Location/Qualifiers
source                  1..8
                        mol_type = protein
                        organism = Lama glama SEQUENCE: 19
ASGRTTYT                                                                 8

SEQ ID NO: 20           moltype = AA  length = 8
FEATURE                 Location/Qualifiers
source                  1..8
                        mol_type = protein
                        organism = Lama glama SEQUENCE: 20
IIPTGGTI                                                                 8

SEQ ID NO: 21           moltype = AA  length = 17
FEATURE                 Location/Qualifiers
source                  1..17
                        mol_type = protein
                        organism = Lama glama SEQUENCE: 21
ALKISGPVTT LQEDYDY                                                       17

SEQ ID NO: 22           moltype = AA  length = 8
FEATURE                 Location/Qualifiers
source                  1..8
                        mol_type = protein
                        organism = Lama glama

SEQUENCE: 22
```

-continued

```
GSTVIDYA                                                          8

SEQ ID NO: 23          moltype = AA   length = 8
FEATURE                Location/Qualifiers
source                 1..8
                       mol_type = protein
                       organism = Lama glama

SEQUENCE: 23
IDSNGRRT                                                          8

SEQ ID NO: 24          moltype = AA   length = 16
FEATURE                Location/Qualifiers
source                 1..16
                       mol_type = protein
                       organism = Lama glama SEQUENCE: 24
AAGNRGPRDD IGQYYY                                                 16

SEQ ID NO: 25          moltype = AA   length = 8
FEATURE                Location/Qualifiers
source                 1..8
                       mol_type = protein
                       organism = Lama glama

SEQUENCE: 25
ESTLDNYA                                                          8

SEQ ID NO: 26          moltype = AA   length = 8
FEATURE                Location/Qualifiers
source                 1..8
                       mol_type = protein
                       organism = Lama glama

SEQUENCE: 26
ITKGGSFV                                                          8

SEQ ID NO: 27          moltype = AA   length = 16
FEATURE                Location/Qualifiers
source                 1..16
                       mol_type = protein
                       organism = Lama glama SEQUENCE: 27
AAKRSYYVCS PDDYDY                                                 16

SEQ ID NO: 28          moltype = AA   length = 8
FEATURE                Location/Qualifiers
source                 1..8
                       mol_type = protein
                       organism = Lama glama

SEQUENCE: 28
GPTGFITG                                                          8

SEQ ID NO: 29          moltype = AA   length = 7
FEATURE                Location/Qualifiers
source                 1..7
                       mol_type = protein
                       organism = Lama glama

SEQUENCE: 29
LFNSGTT                                                           7

SEQ ID NO: 30          moltype = AA   length = 13
FEATURE                Location/Qualifiers
source                 1..13
                       mol_type = protein
                       organism = Lama glama SEQUENCE: 30
NIIRMYDSRR YSD                                                    13

SEQ ID NO: 31          moltype = AA   length = 8
FEATURE                Location/Qualifiers
source                 1..8
                       mol_type = protein
                       organism = Lama glama

SEQUENCE: 31
GIAFSIYA                                                          8

SEQ ID NO: 32          moltype = AA   length = 7
FEATURE                Location/Qualifiers
source                 1..7
                       mol_type = protein
                       organism = Lama glama
```

-continued

```
SEQUENCE: 32
ITSGAST                                                                     7

SEQ ID NO: 33          moltype = AA  length = 9
FEATURE                Location/Qualifiers
source                 1..9
                       mol_type = protein
                       organism = Lama glama
SEQUENCE: 33
NAKFLGLDY                                                                   9

SEQ ID NO: 34          moltype = AA  length = 8
FEATURE                Location/Qualifiers
source                 1..8
                       mol_type = protein
                       organism = Lama glama
SEQUENCE: 34
ASGRTTYT                                                                    8

SEQ ID NO: 35          moltype = AA  length = 8
FEATURE                Location/Qualifiers
source                 1..8
                       mol_type = protein
                       organism = Lama glama
SEQUENCE: 35
ISPTGGTI                                                                    8

SEQ ID NO: 36          moltype = AA  length = 17
FEATURE                Location/Qualifiers
source                 1..17
                       mol_type = protein
                       organism = Lama glama
SEQUENCE: 36
ALKISGPVTT LEEDYDY                                                          17

SEQ ID NO: 37          moltype = AA  length = 8
FEATURE                Location/Qualifiers
source                 1..8
                       mol_type = protein
                       organism = Lama glama
SEQUENCE: 37
GFDSAYYV                                                                    8

SEQ ID NO: 38          moltype = AA  length = 8
FEATURE                Location/Qualifiers
source                 1..8
                       mol_type = protein
                       organism = Lama glama
SEQUENCE: 38
IGTSSGTT                                                                    8

SEQ ID NO: 39          moltype = AA  length = 17
FEATURE                Location/Qualifiers
source                 1..17
                       mol_type = protein
                       organism = Lama glama
SEQUENCE: 39
ALANRWYPTL VRHDYLF                                                          17

SEQ ID NO: 40          moltype = AA  length = 8
FEATURE                Location/Qualifiers
source                 1..8
                       mol_type = protein
                       organism = Lama glama
SEQUENCE: 40
GFTSSNYR                                                                    8

SEQ ID NO: 41          moltype = AA  length = 8
FEATURE                Location/Qualifiers
source                 1..8
                       mol_type = protein
                       organism = Lama glama
SEQUENCE: 41
RTGAGGAT                                                                    8

SEQ ID NO: 42          moltype = AA  length = 14
FEATURE                Location/Qualifiers
source                 1..14
                       mol_type = protein
```

-continued

```
                           organism = Lama glama
SEQUENCE: 42
YYCNAFDSEN QNNY                                                            14

SEQ ID NO: 43             moltype = AA   length = 8
FEATURE                   Location/Qualifiers
source                    1..8
                          mol_type = protein
                          organism = Lama glama
SEQUENCE: 43
AFTSSNYR                                                                   8

SEQ ID NO: 44             moltype = AA   length = 8
FEATURE                   Location/Qualifiers
source                    1..8
                          mol_type = protein
                          organism = Lama glama
SEQUENCE: 44
RTGAGGAT                                                                   8

SEQ ID NO: 45             moltype = AA   length = 14
FEATURE                   Location/Qualifiers
source                    1..14
                          mol_type = protein
                          organism = Lama glama
SEQUENCE: 45
YYCNAIDFEN QNNY                                                            14

SEQ ID NO: 46             moltype = AA   length = 8
FEATURE                   Location/Qualifiers
source                    1..8
                          mol_type = protein
                          organism = Lama glama
SEQUENCE: 46
GFTASNYR                                                                   8

SEQ ID NO: 47             moltype = AA   length = 8
FEATURE                   Location/Qualifiers
source                    1..8
                          mol_type = protein
                          organism = Lama glama
SEQUENCE: 47
RNGPGGRT                                                                   8

SEQ ID NO: 48             moltype = AA   length = 14
FEATURE                   Location/Qualifiers
source                    1..14
                          mol_type = protein
                          organism = Lama glama
SEQUENCE: 48
YYCNAIDMGN SNAY                                                            14

SEQ ID NO: 49             moltype = AA   length = 8
FEATURE                   Location/Qualifiers
source                    1..8
                          mol_type = protein
                          organism = Lama glama
SEQUENCE: 49
AFTSSNYR                                                                   8

SEQ ID NO: 50             moltype = AA   length = 8
FEATURE                   Location/Qualifiers
source                    1..8
                          mol_type = protein
                          organism = Lama glama
SEQUENCE: 50
RTGAGGAT                                                                   8

SEQ ID NO: 51             moltype = AA   length = 14
FEATURE                   Location/Qualifiers
source                    1..14
                          mol_type = protein
                          organism = Lama glama
SEQUENCE: 51
YYCNAIDFEN QSNY                                                            14

SEQ ID NO: 52             moltype = AA   length = 8
FEATURE                   Location/Qualifiers
source                    1..8
```

-continued

```
                             mol_type = protein
                             organism = Lama glama
SEQUENCE: 52
AFTSSNYR                                                          8

SEQ ID NO: 53                moltype = AA   length = 8
FEATURE                      Location/Qualifiers
source                       1..8
                             mol_type = protein
                             organism = Lama glama
SEQUENCE: 53
RTGAGGAT                                                          8

SEQ ID NO: 54                moltype = AA   length = 14
FEATURE                      Location/Qualifiers
source                       1..14
                             mol_type = protein
                             organism = Lama glama
SEQUENCE: 54
YYCNAIDFEN QTNY                                                  14

SEQ ID NO: 55                moltype = AA   length = 8
FEATURE                      Location/Qualifiers
source                       1..8
                             mol_type = protein
                             organism = Lama glama
SEQUENCE: 55
GFTSNNYR                                                          8

SEQ ID NO: 56                moltype = AA   length = 8
FEATURE                      Location/Qualifiers
source                       1..8
                             mol_type = protein
                             organism = Lama glama
SEQUENCE: 56
RTGAGGAT                                                          8

SEQ ID NO: 57                moltype = AA   length = 14
FEATURE                      Location/Qualifiers
source                       1..14
                             mol_type = protein
                             organism = Lama glama
SEQUENCE: 57
YYCNAFDSEN QSNY                                                  14

SEQ ID NO: 58                moltype = AA   length = 8
FEATURE                      Location/Qualifiers
source                       1..8
                             mol_type = protein
                             organism = Lama glama
SEQUENCE: 58
GLTFSDYD                                                          8

SEQ ID NO: 59                moltype = AA   length = 8
FEATURE                      Location/Qualifiers
source                       1..8
                             mol_type = protein
                             organism = Lama glama
SEQUENCE: 59
KASADGRT                                                          8

SEQ ID NO: 60                moltype = AA   length = 13
FEATURE                      Location/Qualifiers
source                       1..13
                             mol_type = protein
                             organism = Lama glama
SEQUENCE: 60
NARRNWGGRP QDY                                                   13

SEQ ID NO: 61                moltype = AA   length = 15
FEATURE                      Location/Qualifiers
source                       1..15
                             mol_type = protein
                             organism = synthetic construct
SEQUENCE: 61
GGGGSGGGGS GGGGS                                                 15
```

CONJUGATE OR FUSION PROTEIN FOR CANCER THERAPY

REFERENCE TO SEQUENCE LISTING, TABLE OR COMPUTER PROGRAM

This application contains an ST.26 compliant Sequence Listing, which is submitted concurrently in xml format via EFS-Web or Patent Center and is hereby incorporated by reference in its entirety. The .xml copy, created on Sep. 7, 2022 is named SequenceListing.xml and is 52.3 KB in size.

FIELD OF THE INVENTION

The present invention relates to a conjugate or a fusion protein comprising an antibody against TREM (triggering receptors expressed on myeloid cells) like transcript-1 (TLT-1) and a cytotoxic molecule. Such conjugate or fusion protein is directed to activated platelets that are associated with the tumor cell microenvironment and release the cytotoxic molecule to generate local killing of surrounding target tumor cells. The present invention also provides single domain antibodies (sdAbs) against mouse and/or human TLT-1.

BACKGROUND OF THE INVENTION

Tumor microenvironment (TME) is the environment around a tumor, including the surrounding blood vessels, blood cells, including red/white cells and platelets, stromal cells, including carcinoma associated fibroblasts (CAFs) and the extracellular matrix (ECM), and actively interacts with the tumor and promotes cancer progression. Immune checkpoint blockade was the first TME-based tumor therapies, such as CTLA4 and PD1. Patients who respond to immune checkpoint blockade therapy have seen significant clinical benefit, however, most patients are unresponsive. Targeting other TME cells, for example, tumor-associate macrophages (TAM), CAFs and ECM have gained considerable interest in cancer therapeutic research, but limited successes have been achieved due to their highly complex and heterogeneous features (Rodrigues et al., Int. J. Mol. Sci. 2019, 20, 840; Bejarano et al., Cancer Discovery 2021, 11, 933).

Another blood component, the platelet, has been studied extensively for its role in TME recently, including not only within a solid tumor mass, but also within a hematogenous micro-metastasis. Platelets are the second most numerous of the circulating blood components and the thrombocytosis is remarkably associated with the poor prognosis in a variety of solid cancers. Tumor-induced thromboembolism is the second leading cause of death in cancer patients and clinically related to tumor-induced platelet activation and blood coagulation. At the site of a primary tumor, the blood components reach the TME via leaky blood vessels, whose permeability is increased by tumor-secreted growth factors. For cancer cells that circulate in the blood stream, platelets are recruited primarily by direct cell-cell interactions via different receptor/counter receptor pairs, such as CLEC-2/podoplanin, P-selectin/PSGL-1, and indirectly by fibrin, which bridges the two cell types via αIIβIII/αVβ3. (Palacios-Acedo et al., Frontiers in Immunology 2019, 10, 1805; Palacios-Acedo et al., Cancers 2022, 14, 730; Chapelain et al., 2022, 14, 2192; Varkey et al., Cureus 2021, 13, 1).

Resting platelets normally circulate in blood, ready to provide a matrix for procoagulant factor complex assembly when blood vessels and their subendothelial compartments are injured. The interaction of platelets and injured sites initiates platelet adhesion, aggregation and activation as well as distinct changes to platelet shape and composition that support procoagulant factor binding to the activated platelet membrane surface. At the same time, activation of platelets directly releases a number of molecular species from storage granules that further support platelet function, including ultra-large molecular species, like von Willebrand factor (vWF) and fibrin, that help to form a stabilizing meshwork at the site of injury, and adhesion molecules, like P-selectin, TLT-1, and others that promote cellular interaction. Such a molecular meshwork, in addition to many other molecular species, like growth factors, secreted by activated platelets, tumor cells, and the like, help promote localized binding of tumor cells and establish a framework for their attachment and growth, and possibly, dispersion throughout the body; this may be especially true for circulating tumors cells that are likely to have metastatic potential (Tesfamariam et al. Pharmacology and Therapeutics, 2016, 157, 112). Ultimately, this attractive microenvironment may also allow escape of tumors from immune cell surveillance.

Tumor cells are inherently heterogeneous and are capable of eliciting the expression of molecules with a variety of activities. These include generation of thrombin, a potent activator of platelets, that is likely produced as a result of constitutive expression of tissue factor on most tumor cells (Lambert et al., Cell 2017, 168, 670). This results in a continuous cycle of platelet activation, procoagulant assembly and further thrombin generation with resulting repeated activation of new platelets. Formation of thrombin-rich and platelet-rich emboli may be critical in promoting metastases whereby thrombin-activated platelets and tumor cells interact with each other to form platelet-tumor emboli and, in so doing, prolong tumor survival in the circulation. It is these metastatic growths that represent the greatest obstacle to treating cancer effectively. In addition to thrombin, tumor cells, as well as other infiltrating cells of tumors, produce a variety of other substances that activate platelets (Palacios-Acedo et al., Frontiers in Immunology 2019, 10, 1805).

While targeting with approved drugs may represent a method for dealing with platelets, they generally do not have the appropriate attributes to eliminate associated cancers. Aspirin has been touted to have some benefit in certain cancers, like colorectal and breast cancer (Cao et al., JAMA Oncology 2016, 2, 762; Lie et al, Medicine 2021, 100, e26870) but few others have achieved this notoriety. A potential therapeutic benefit to the observation that platelets and tumor cells are in close association is the fact that the exceedingly selective expression of certain molecules that are present only on activated platelets can be used to exquisitely target antitumor drugs to them with a resulting effect of collateral killing of associated tumor cells.

TREM (triggering receptors expressed on myeloid cells), like transcript-1 (TLT-1) molecules, are released from platelet α-granules upon activation by platelet stimulants (Washington et al., Blood 2004, 104, 1042). TLT-1 is expressed at high levels on the platelet surface (15,000-50,000 molecules/platelet), depending on the activation method (Smith et al., Blood Advance 2018; 2, 2072, Branfield et al., Platelets, 2021, 32, 753).

One class of targeting agents have payloads comprised of toxic and potent molecules derived from maytansinoids, auristatins/dolastatins, calicheamicins, microcystin, and cyanotoxins, for example. When these types of molecules are attached to antibodies, they are designated as antibody-drug conjugates or ADCs. Due to their extremely toxic nature and very short half-life as stand-alone molecules, several of these have been prepared as conjugates with antibodies that target specific proteins on tumor cells; some of these have further progressed into the clinic (Johanssen et al., *Scientific Reports*, 2017, 7, 15920).

Unfortunately, each tumor or tumor type expresses different cell surface molecules, making it difficult to predict what the nature of the targeting antibody should be—for example, breast tumors are often targeted with antibodies against the HER-2/neu receptor but this receptor is limited to only about 30% of breast tumors. As a result, a substantial number of different conjugates would need to be prepared in order to cover the vast array of receptors and receptor combinations that exist on breast and other tumor types, especially if a single target cannot be identified. This scenario seems impractical given the heterogeneity of tumors and the diversity of proteins they express.

Interleukin-2 is already used as a stand-alone drug (Proleukin®/aldesleukin) for treatment of metastatic melanoma and metastatic kidney cancers; however, it has considerable side-effects when used systemically. Because of the complexities associated with IL-2 binding to its various α, β and γ receptor subunits, there has been considerable effort placed on identifying variants of IL-2 that have the potential to attenuate signaling and thus differentially affect lymphocyte activation and biological function (Mitra et al., *Immunity*, 2015, 42, 826).

Waldhauer et al., (*MABS* 2121, 13, e1913791) have tried to use IL-2 fused to antibodies directed against tumor antigens. This approach is fraught with considerable difficulty due to the large complexity and diversity of antigens present on tumors.

BRIEF DESCRIPTION OF THE DRAWINGS

FIG. 1B depicts the amino acid sequences of CDR1, CDR2 and CDR3, of 20 anti-TLT-1 antibodies (SEQ ID NO: 1-60) of the present invention.

4 directly to cancer cells (all n=3). (B) Analysis of the region of cancer cells positive for CD62P (purple), confirming that platelets can bind directly to cancer cells (all n=3), and all platelets (100%) associated with the cancer cells are activated. (C) Analysis of the region of cancer cells positive for TLT-1 HcAb, confirming that platelets binding to cancer cells are activated (all n=3) and TLT-1 receptors are expressed on the activated platelet surface as shown by positive staining with TLT-1 HcAb.

Figure 4:
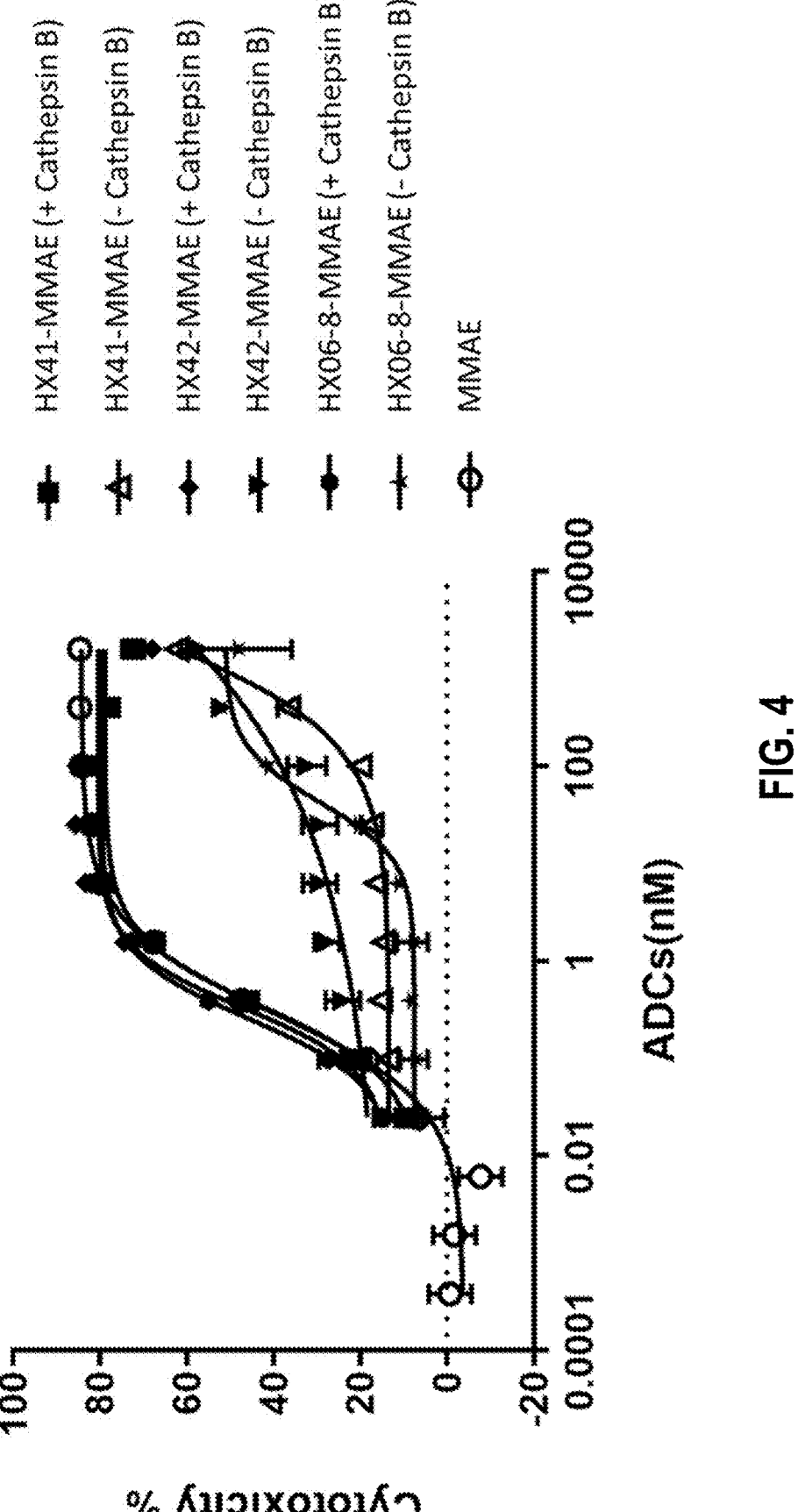

FIG. 4 demonstrates that tumor microenvironment (TME)-enriched Cathepsin B can effectively cleave the linker to active the prodrug MMAE. The cytotoxic activity of MMAE on tumor cells after 96 hours of incubation was assessed in a cell culture assay with (+C) and without (−C) Cathepsin B; the results indicated that effective killing of triple-negative breast adenocarcinoma cells, MDA-MB-231, by anti-TLT HcAb-MMAE (2 TLT-1 HcAb-MMAE ADC molecules: HX41-MMAE and HX42-MMAE), and anti-GFP HcAb-MMAE, only occurred in the presence of Cathepsin B; this confirmed that the conjugation of MMAE to the HcAb was as expected (as outlined in FIG. 2); in addition, it supports the hypothesis that is controlled release active MMAE upon exposure to Cathepsin B in TME to inhibit tumor growth. Data points represent group mean, and error bars represent standard error of the mean (SEM), n=8.

Figure 5:
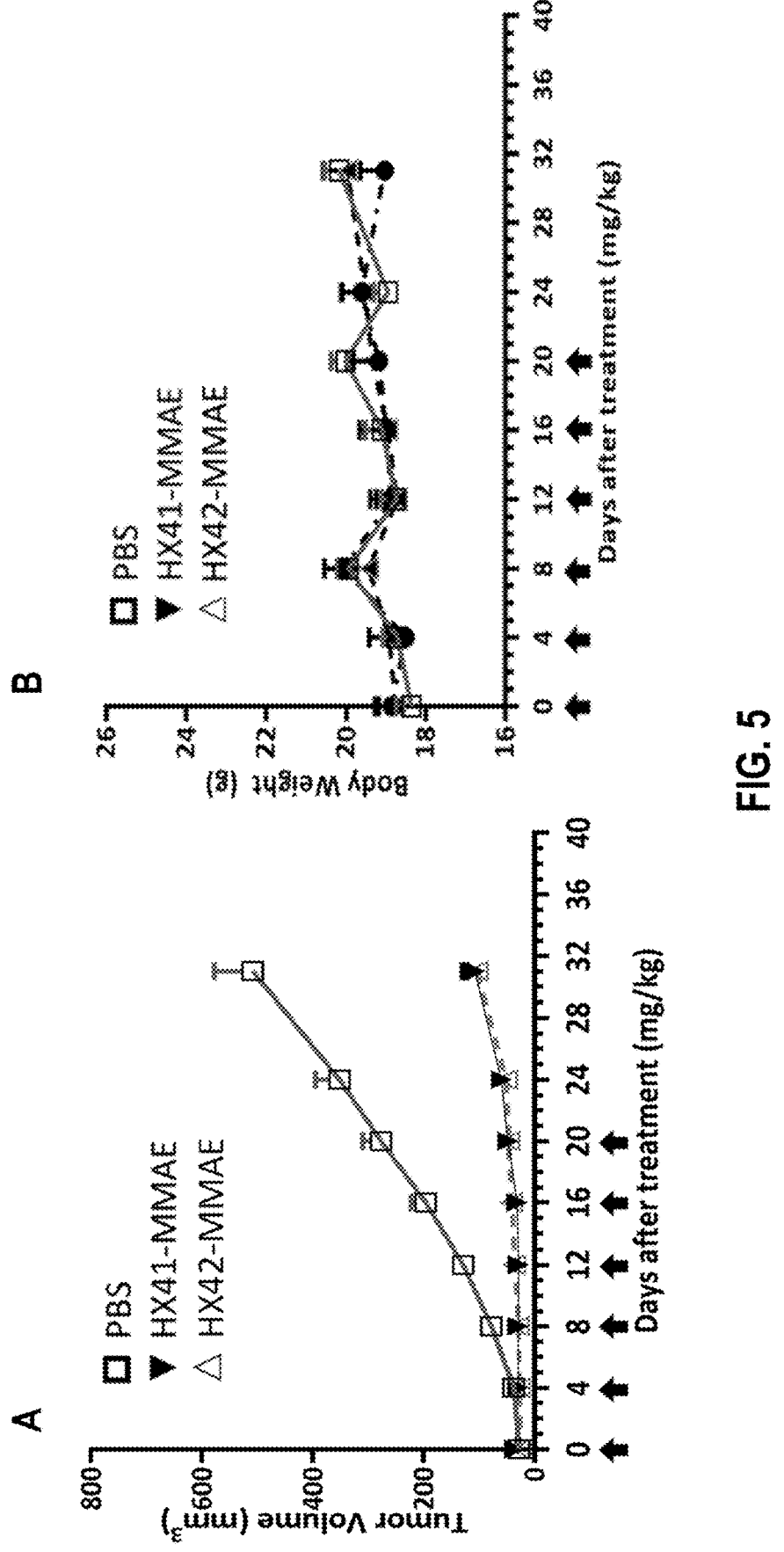

FIG. 5 illustrates that a targeted TLT-1 HcAb-MMAE construct could effectively inhibit tumor growth. A MDA-MB-231 tumor model was used to evaluate the therapeutic efficacy of two TLT-1 HcAb-MMAE molecules (HX-41-MMAE and HX-42-MMAE). When the tumor size reached 50 mm³, 6 mg/kg of each TLT-1 HcAb-MMAE were injected intravenously into animals every four days for a total of six times; phosphate-buffered saline (PBS) was used as control. Panel A shows that TLT-1 HcAb-MMAE drugs effectively inhibit the tumor growth for more than 80% compared to PBS negative control at 32 days and without observable body weight loss (Panel B). Data points represent group mean, and error bars represent standard error of the mean (SEM), n=8.

Figure 6:
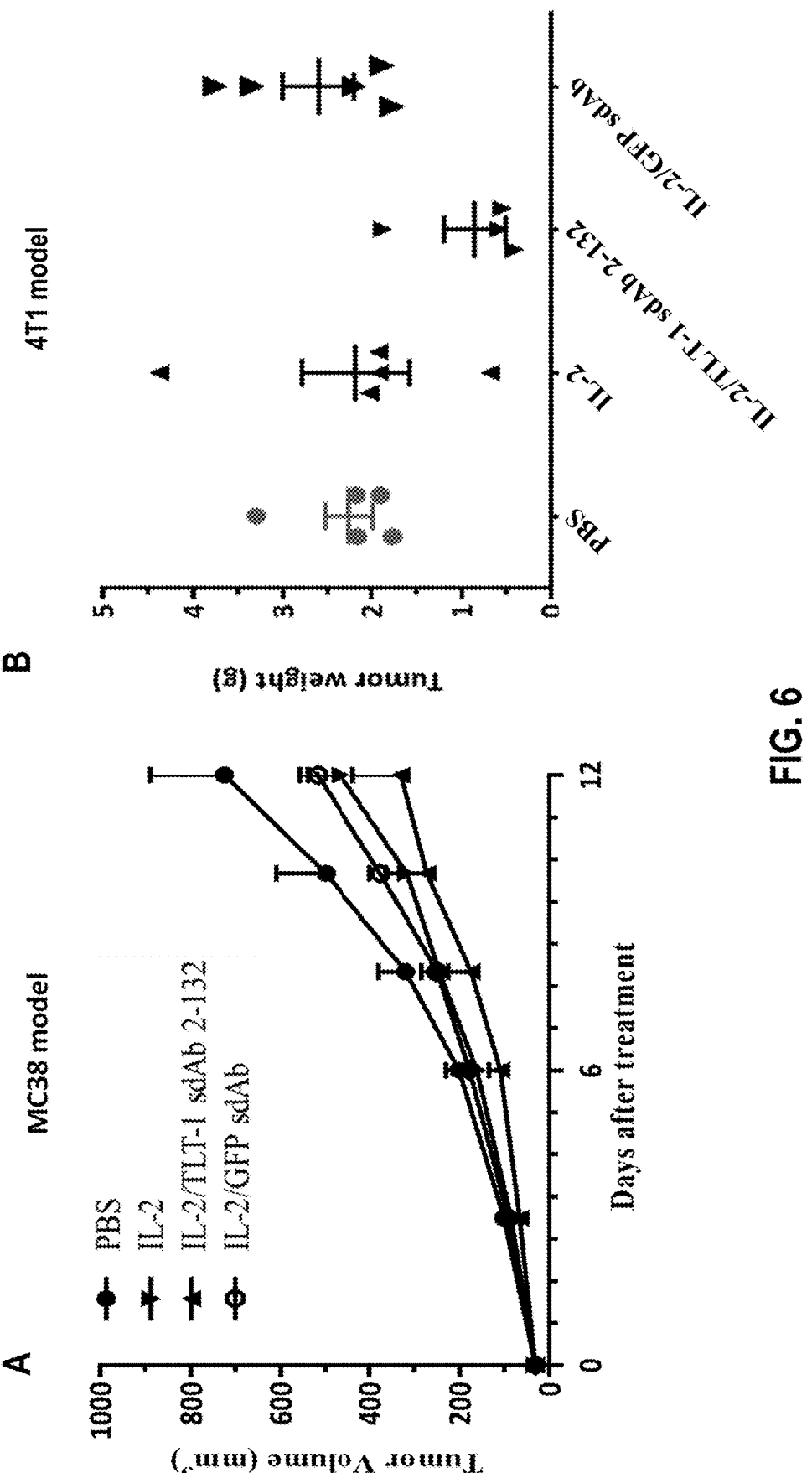

FIG. 6 shows that a targeted TLT-1 sdAb-IL2 fusion construct effectively inhibited tumor growth. Two syngeneic mouse tumor models, MC-38 (colorectal) and 4T1 (breast), were used to evaluate the therapeutic efficacy of TLT-1 sdAb-IL2 fusion molecules. When the tumor sizes reached 50 mm 3, equimolar (0.15 nM) amounts of TLT-1 sdAb-IL-2, GFP sdAb-IL-2 or IL-2 were injected intravenously into animals every day. The results show that the TLT-1 sdAb-IL2 fusion could effectively inhibit MC-38 (A) and T41(B) tumor growth at 12 days compared to a non-targeted, negative control. Data points represent group mean, and error bars represent standard error of the mean (SEM), n=6.

Figures 7A, 7B:
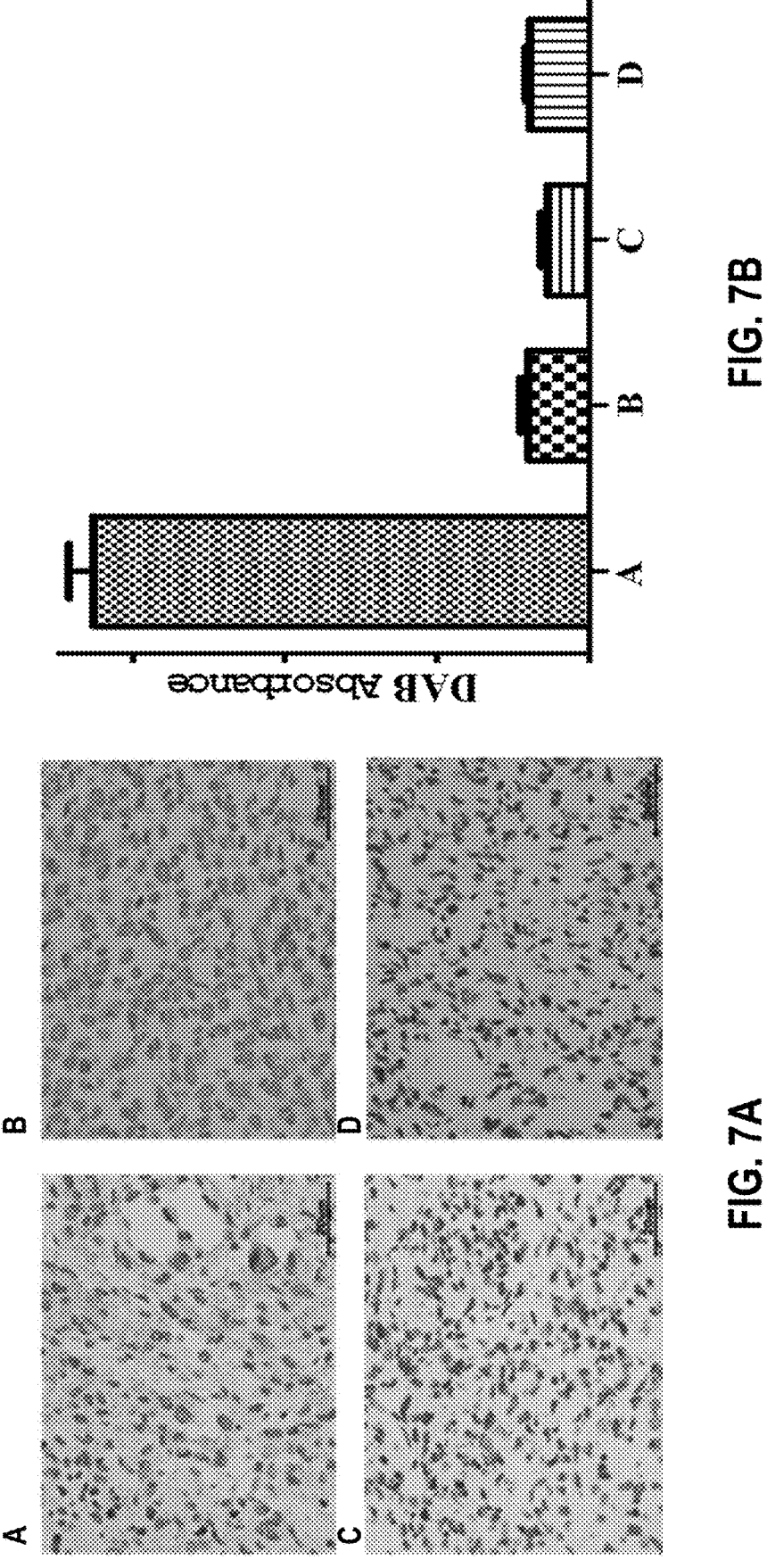

FIGS. 7A and 7B depict the TLT-1-targeted association of platelets with MDA-MB-231 tumor cells. At the end of the in-life animal studies, tumors were removed from animals and fixed in formalin. (A) The tumor sections were incubated with anti-TLT-1 HcAb AHP11983 (a), followed with an HRP-coupled goat anti-human Fc antibody. A non-target HcAb NX06-8 (b) and HRP conjugated goat anti-human Fc antibody (c), and DAB only (d), samples were used as controls; DAB or diaminobenzidine was used as a substrate for HRP. Photomicrographs were taken at 400× magnification; scale bar=20 μm. The average DAB intensity of each tumor section was obtained using Image Pro Plus 6 image scanning software. The experiments were performed using five independent samples in each group. The results demonstrated that the anti-TLT-1 HcAb can specifically recognize the activated platelets in a tumor microenvironment compared to controls. (B) Digital imaging software was used to convert the dye absorbance into pixels for the calculation of the number of activated platelets represented by DAB staining. The DAB intensity of each tumor section IHC were compared, and the quantification was derived from the staining of five independent sections. Nanobody stained IHC sections of (a) AHP11983, (b) NX06-8, (c) HRP-anti-Fc/DAB, and (d) DAB at 400× magnification.

Figures 8A, 8B:
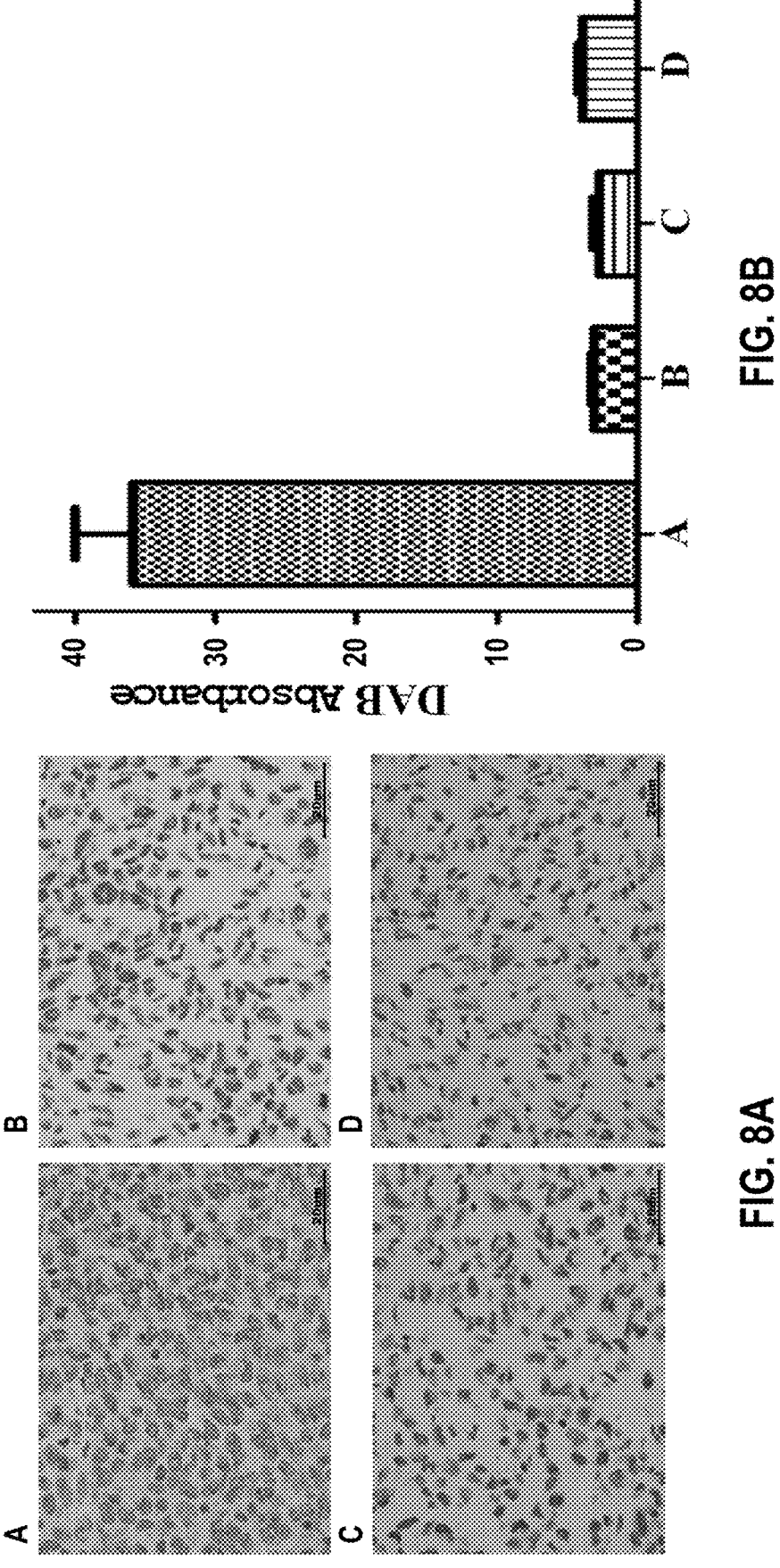

FIGS. 8A and 8B depict the TLT-1 targeted association of platelets with 4T1 tumor cells. At the end of the in-life animal studies, tumors were removed from animals and fixed in formalin. (A) The tumor sections were incubated with anti-TLT-1 HcAb AHP11983 (a), followed with an HRP-coupled goat anti-human Fc antibody. A non-target HcAb NX06-8 (b) and HRP conjugated goat anti-human Fc antibody (c), and DAB only (d), samples were used as controls; DAB or diaminobenzidine was used as substrate for HRP. Photomicrographs were taken at 400× magnification; scale bar=20 μm. The average DAB intensity of each tumor section was obtained using Image Pro Plus 6 image scanning software. The experiments were performed using five independent samples in each group. The results demonstrated that the anti-TLT-1 HcAb can specifically recognize the activated platelets in a tumor microenvironment compared to controls. (B) Digital imaging software was used to convert the dye absorbance into pixels for the calculation of the number of activated platelets represented by DAB staining. The DAB intensity of each tumor section IHC were compared, and the quantification was derived from the staining of five independent sections. Nanobody stained IHC sections of (a) AHP11983, (b) NX06-8, (c) HRP-anti-Fc/DAB, and (d) DAB are shown at 400× magnification.

DETAILED DESCRIPTION OF THE INVENTION

Definitions

"ADC" (antibody-drug conjugate) refers to either a small anti-neoplastic, anti-mitotic, chemotherapeutic or other potent molecule that kills cells and is attached, often through a linker (peptide or other) to an antibody—antibodies can be of any variety, including full-length, Fab, Fv (monomeric, dimeric, trimeric, etc.), sdAb, HcAb and other more elaborate types.

An "anti-mitotic agent" is a type of molecule that blocks cell growth by stopping mitosis (cell division). Classic anti-mitotics are called "microtubule poisons", as they bind to microtubules and block their polymerization dynamics. For example, anti-mitotic agents include taxanes (paclitaxel and its derivatives) and vinca alkaloids (vinblastine, vincristine and their derivatives).

An "anti-neoplastic agent" refers to a molecule that damages DNA and blocks the formation of neoplasms (growth that may become cancer). An "anti-neoplastic agent" is also called an anti-cancer agent, chemotherapy agent, chemo agent, or cytotoxic agent.

"CDRs" are complementary determining Regions of VH or VL chains of antibody which are critical for binding with antigen.

A "conjugate" is a complex formed from the joining together of two or more molecules by covalent bond.

"Cytokines" are proteins (typically ~5000-25,000 daltons) that modulate cell signaling. Cytokines are peptides and cannot cross the lipid bilayer of cells to enter the cytoplasm. Cytokines include chemokines, interferons, interleukins, lymphokines, and tumor necrosis factors. Cytokines generally modulate a positive or negative cellular effect by interacting with another molecule, often on the cell surface.

A "domain" means one region in a polypeptide which is folded into a particular structure independently of other regions.

A "fusion protein" is a protein consisting of at least two domains that are encoded by separate genes that have been joined so that they are transcribed and translated as a single unit, producing a single polypeptide.

A "single domain antibody" (sdAb), or a "variable domain of heavy chain antibody" (VHH), also known as a nanobody, is an antibody fragment consisting of a single monomeric variable antibody, i.e., a variable domain of a heavy chain of an antibody. A single domain antibody is typically derived from the Camelidae family. VHH and sdAb are used interchangeably in this application.

A "heavy chain-only antibody" (HcAb), is an immunoglobulin comprising only the variable and constant region domains of the heavy chain of certain animals, typically derived from the Camelidae family. In some cases, the camelid constant regions may be replaced with a human equivalent, comprising the hinge, CH2 and CH3 heavy chain domains; in such cases, this format is referred to as a chimeric, humanized HcAb or "chHcAb".

"TREM (triggering receptors expressed on myeloid cells) like transcript-1" (TLT-1), as used herein, is a membrane protein receptor found only in alpha-granules of platelets and megakaryocytes. TLT-1 contains an extracellular V-set Ig domain, a proline-rich region, and an immune receptor tyrosine-based inhibitory motif in its cytoplasmic tail. Upon platelet activation, TLT-1 is rapidly brought to the surface of platelets where it can enhance $Ca^{++}$ influx and promote platelet aggregation.

The inventor has discovered platelets as a targeting site in the microenvironment of tumors and designed conjugates or fusion proteins with appropriate molecular payloads to reach the target site to effectively attack and kill tumors.

The present invention relates to conjugates and fusion proteins comprising a payload covalently linked to an antibody against TREM (triggering receptors expressed on myeloid cells) like transcript-1 (TLT-1) molecules that are present on activated platelets at the site of an injury. The payload is typically a cytotoxic moiety or molecule attached to an antibody; it is referred to as a 'payload' as it is the functional aspect of the conjugates or fusion proteins that lead to killing or cytotoxicity. Such conjugates or fusion proteins are directed to activated platelets that are associated with the tumor cell microenvironment. The tumor-associated platelets (TAP) provide a selective platform for targeted delivery of moieties which payloads are then released and generate local killing, directly or indirectly, of surrounding target tumor cells. Selective targeting provides an effective, selective and reliable means for killing tumors.

In a first aspect, the present application provides a conjugate or a fusion protein comprising an anti-TLT-1 antibody and a payload; wherein the anti-TLT-1 antibody and the drug are covalently linked together, and the payload is an anti-neoplastic molecule, anti-mitotic molecule, a transcription or translation inhibitor, or a cytokine. The conjugate directs and delivers the drug only to activated platelets in the context of tumor microenvironments. The conjugate targets TREM-like transcript-1 (TLT-1) molecules that are released from platelet α-granules upon activation by platelet stimulants. As a single chain molecule, TLT-1 is sequestered in α-granules and it does not appear on the surface of platelets until activated. TLT-1 does not exist in an inactivated form on resting platelets, and it does not have the potential to form heterodimers with other proteins.

Continual activation of platelets in a tumor microenvironment provides an excellent milieu for molecular targeting by a high-affinity antibody against TLT-1 protein on activated platelets, especially for solid tumors where the excellent tissue penetration feature of sdAb is critical.

The anti-TLT-1 antibody in the conjugate is a high-affinity antibody that binds to mouse and/or human TLT-1 proteins on activated, but not resting platelets. In a preferred embodiment, the anti-TLT-1 antibody bind to both human and mouse TLT-1 proteins.

The anti-TLT-1 antibody, as used in this application, may be an antibody or an antigen-binding fragment thereof. For example, the anti-TLT-1 antibody includes a full-length antibody, a monoclonal antibody, a bi-specific monoclonal antibody, Fab, Fv (monomeric, dimeric, trimeric, etc.), a heavy chain antibody (HcAb), a single domain antibody (sdAb), sdAb based heavy chain-only antibody (HcAb), or bivalent/trivalent sdAb (by connecting two or three sdAbs).

The antibody is preferably chimeric or humanized. In one preferred embodiment, sdAbs or chHcAbs are used to prepare the conjugate due to their excellent penetration rate, smaller size, elevated stability, larger number of accessible epitopes, relatively low production costs and improved robustness.

In one embodiment, the conjugate is an ADC, which comprises a payload of an anti-neoplastic molecule, an anti-mitotic molecule, or a transcription or translation inhibitor. Such payload molecules typically have a molecular weight of less than 2000 daltons, or less than 1000 Daltons.

Anti-neoplastic molecules include, but are not limited to, Calicheamicins, CC-1065 analogs, Duocarmycins, and other toxins damaging DNAs. For example, anti-neoplastic molecules suitable for the present conjugate include T-Dxd (exatecan-derivative of topoisomerase I inhibitor), PBD (pyrrobenzodiazepine) and IBD (indolinobenzodiazepine).

Anti-mitotic molecules include maytansinoids, auristatins, taxoids, and other toxins targeting tubulin filaments. Anti-mitotic molecules suitable for the present conjugate include MMAE (monomethyl auristatin E), MMAF (monomethyl auristatin F); dolastatin 10, and maytansinoids derivatives of DM1 (N2'-deacetyl-N2-(3-mercapto-1-oxopropyl)-maytansine) and DM4 (N2-Deacetyl-N2-(4-mercapto-4-methyl-1-oxopentyl)-maytansine).

Transcription inhibitors include, but are not limited to, naturally occurring amatoxins. Transcription inhibitors suitable for the present conjugate include HDP-01 (amanitin), CX-5461, BMH-21 and TAS-106. Translation inhibitors include trabedersen, AZD4785, Omacetaxine, and silbestrol.

The conjugate preferably further comprises a linker between the anti-TLT-1 antibody and the anti-neoplastic molecule. The linker may be in a size of 10-100 Å. The linker preferably comprises a protease cleavage site. Preferably, the protease is a tumor-expressed and upregulated at sites surrounding tumors. For example, the protease includes Cathepsin B, MMP-2 (matrix metalloproteinase 2, also known as Gelatinase A), MMP-9 (matrix metalloproteinase 2, also known as Gelatinase B), legumain, DPP (dipeptidyl protease 4), prostate-specific antigen (PSA), renin, napsin A, and Granzyme B.

Figure 2:
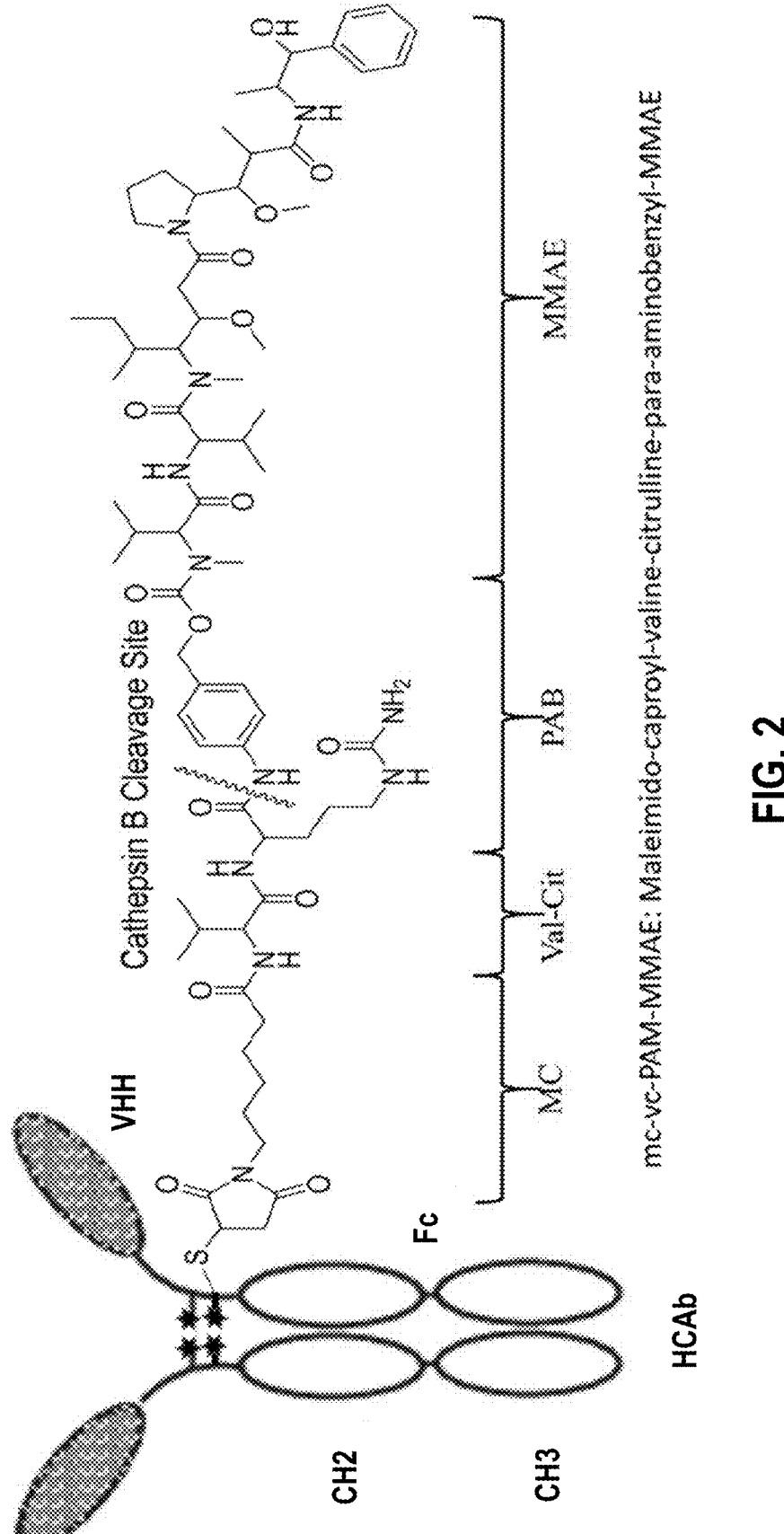
FIG. 2 illustrates the structure of an antibody-drug conjugate. The structure of Monomethyl Auristatin E (MMAE) conjugated via Cathepsin B cleavable linker to an anti-TLT-1 HcAb. As many as four MMAE molecules can be accommodated by maleimide-mediated chemical linkage at the reduced interchain disulfides of the HcAb. The free cysteines are formed during partial reduction using Tris (2-carboxyethyl) phosphine (TCEP) and the reduced HcAb is conjugated with the mc-vc-PAB-MMAE linker in the presence of DMA. The drug antibody ratio (DAR) is confirmed with LC-MS.

FIG. 2 shows an example of a linker with three main subunits used to create the antibody-drug conjugate. The first subunit is an attachment unit which is suitable for conjugation to the antibody at the reduced interchain disulfide bond. The second subunit is a release unit which is a cleavable protease-sensitive Val-Cit dipeptide unit liberating the potent cytotoxic warhead once the ADC reaches its intended target in microenvironment. The third subunit is a PAB spacer unit which is used in modulating payload (MMAE) release or distance from antibody.

The conjugate directs a payload such as an anti-neoplastic agent (e.g., MMAE) to a single type of molecule, namely, TLT-1, that is exclusively expressed on activated platelets contained in the microenvironment of primary tumors, as well as their metastases. The close association of tumor cells with platelets allows for enzymatic release of the toxic payload from the single domain antibody bound to TLT-1 around, and eventually into, the tumor, with subsequent killing. This approach solves the issue of defining and creating large numbers of different targeted ADCs that may or may not work against a specific tumor. Directing the present conjugates to activated platelets associated with tumors provides a simple solution to an otherwise almost intractable problem in selecting from a huge diversity of chemotherapeutic options to treat patients with different cancers.

In another embodiment, the fusion protein of the present invention comprises a payload of a cytokine. Cytokines include chemokines, interferons, interleukins, lymphokines, and tumor necrosis factors. In one embodiment, the fusion protein comprises a cytokine, e.g., IL-2, IL-4, IL-10, IL-21, IFN-α, IFN-β and IFN-γ.

One preferred cytokine is interleukin-2 (IL-2). The co-stimulant properties of IL-2 attract immune-stimulated T-cells to recognize and kill adjacent tumors. IL-2 stimulates subsets of immune cells, particularly cytotoxic CD8+ T-cells, to identify and kill tumors. By conjugating the IL-2 to anti-TLT-1, the present fusion protein specifically targets IL-2 or its variants to TLT-1 on activated platelets, and to the tumor microenvironment. Targeting the fusion protein to the tumor environment allows for a greater probability of directing the appropriate immune cell repertoire, and especially cytotoxic T-cells, to the tumor. This approach is better than relying on a more systemic approach that interacts with a larger number of unwanted cells, which may result in killing unwanted cells as collateral damage from the side-effects of the interleukin.

The fusion protein of the present invention optionally comprises a peptide linker in between the anti-TLT-1 antibody and the cytokine protein. The peptide linker, in general, has 2-amino acids, preferably 5-25 or 10-20 amino acids. For example, the linker may be a polyglycine-serine repeat, for example, GGGGSGGGGSGGGGS (SEQ ID NO: 61).

The fusion protein is targeted to activated platelets directly and specifically. This specific targeting delivers potent co-stimulatory molecules, like IL-2, to the tumor microenvironment via its close association with activated platelets. The targeting does not require defining any specific protein on the tumor itself; thus, this targeting is applicable in treating a variety of cancer or tumor types.

In one embodiment, the present invention provides nucleotide sequences encoding the fusion protein. The nucleotide sequences may be included as part of a prokaryotic, fungal, or eukaryotic expression vector for expression in bacterial cells (like *Escherichia coli*), yeast (like *Saccharomyces cerevisiae*), insect cells (like Sf9, Sf21 and High Five), or mammalian cells (for example, Chinese Hamster Ovary (CHO), HEK, BHK). The fusion protein can be expressed in bacteria, yeast, insect cells, or other eukaryotic cells, such as mammalian cells. When domain folding via disulfide bonds is important, mammalian cell expression is a preferred route.

The conjugate or fusion protein of the present invention, optionally, further comprises a tag, e.g., hexanucleotide His tag incorporated at their C-terminus, to facilitate purification and detection.

The conjugate or fusion protein of the present invention targets tumors through binding of the anti-TLT-1 antibody to activated platelets that express the TLT-1 protein on its surface and are juxtaposed to tumors and tumor cells that efficiently use platelets for their growth and proliferation. The mechanism of action is either direct killing by the targeted anti-neoplastic drug or by stimulation of specialized T-cells that recognize foreign antigens on tumors and kill them.

The present invention further provides a pharmaceutical composition comprising the conjugate or the fusion protein of the present invention and a pharmaceutically acceptable carrier.

The present invention also provides a method to treat multiple types of cancers. The method comprises the steps of: administering the conjugate or the fusion protein of the present invention to a subject in need thereof, binding the conjugate or the fusion protein to TLT-1 expressed on the surface of activated platelets in tumor microenvironments, delivering the drug to the tumor, and killing the tumor. All tumor microenvironment has activated platelets;

therefore, the present method which administers a conjugate or a fusion protein comprising an anti-TLT-1 antibody would be effective to target the drug to multiple types of cancers and treat them.

The conjugate or the fusion protein can be administered by intravenous, subcutaneous, oral, nasal, or aerosol route; with intravenous or subcutaneous administration being a preferred route.

Single Domain Antibodies (sdAb) Against TLT-1 (TREM-Like Transcript 1)

TLT-1 (TREM-like transcript 1) protein is expressed selectively on the surface of activated platelets and contains a number of described grooves on its surface; such characteristics make TLT-1 ideally suited for interacting with the single domain antibodies. These surface grooves appear to contain amino acid residues with both negatively-charged and uncharged electrostatic properties that allow interaction with selected amino acids distinctly- and conformationally-displayed on sdAbs.

Figure 1A:
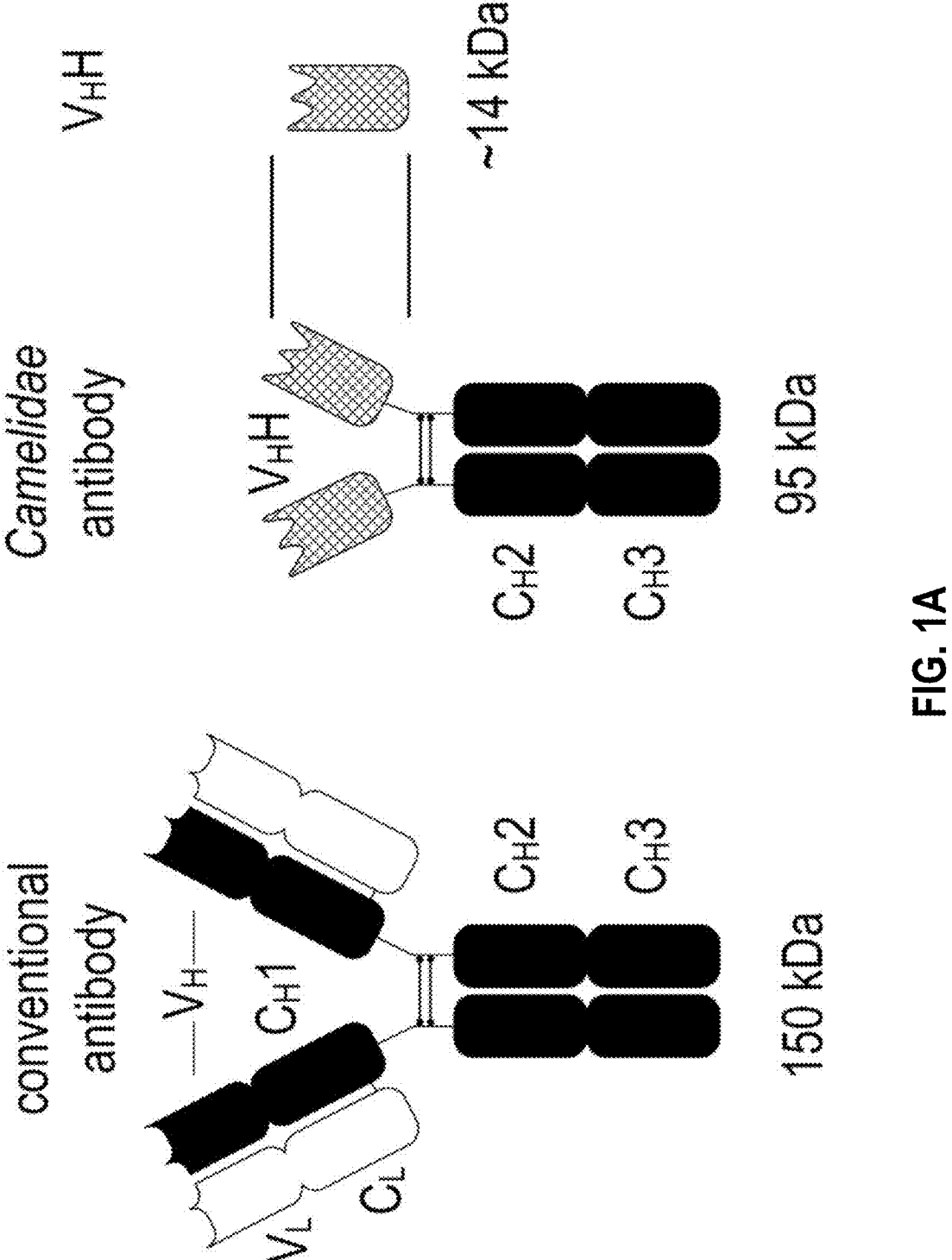
FIG. 1A illustrates the structures of conventional antibody, Camelidae antibody, and VHH. The conventional antibody is a four-polypeptide unit consisting of two identical heavy chains (H) and two identical light chains (L) held together by disulfide bonds to form the Y shape of the antibody and the N-terminal variable region (VH-VL) binds to the antigens. Camelid antibodies lacks a light chain and are composed of only two identical heavy chains, where the VHH domain (also known as sdAb or nanobody) binds the antigen.

The inventors have prepared high-affinity single domain antibodies that target mouse and/or human TLT-1 protein. The inventors have generated a total of 20 sdAb. FIG. 1B shows the CDR sequences of the 20 anti-TLT-1 sdAb sequences. The 20 sdAb were isolated from a llama naïve antibody library (GenScript ProBio). The detail of the sdAb screening procedures is described in US20220041716, which is incorporated herein by reference in its entirety.

In one aspect, the present invention provides a single domain antibody against mouse and/or human TLT-1, comprising: (a) CDR1 being SEQ ID NO: 1, CDR2 being SEQ ID NO: 2, CDR3 being SEQ ID NO: 3; (b) CDR1 being SEQ ID NO: 4, CDR2 being SEQ ID NO: 5, CDR3 being SEQ ID NO: 6; (c) CDR1 being SEQ ID NO: 7, CDR2 being SEQ ID NO: 8, CDR3 being SEQ ID NO: 9; (d) CDR1 being SEQ ID NO: 10, CDR2 being SEQ ID NO: 11, CDR3 being SEQ ID NO: 12; (e) CDR1 being SEQ ID NO: 13, CDR2 being SEQ ID NO: 14, CDR3 being SEQ ID NO: 15; (f) CDR1 being SEQ ID NO: 16, CDR2 being SEQ ID NO: 17, CDR3 being SEQ ID NO: 18; (g) CDR1 being SEQ ID NO: 19, CDR2 being SEQ ID NO: 20, CDR3 being SEQ ID NO: 21; (h) CDR1 being SEQ ID NO: 22, CDR2 being SEQ ID NO: 23, CDR3 being SEQ ID NO: 24; (i) CDR1 being SEQ ID NO: 25, CDR2 being SEQ ID NO: 26, CDR3 being SEQ ID NO: 27; (j) CDR1 being SEQ ID NO: 28, CDR2 being SEQ ID NO: 29, CDR3 being SEQ ID NO: 30; (k) CDR1 being SEQ ID NO: 31, CDR2 being SEQ ID NO: 32, CDR3 being SEQ ID NO: 33; (l) CDR1 being SEQ ID NO: 34, CDR2 being SEQ ID NO: 35, CDR3 being SEQ ID NO: 36; (m) CDR1 being SEQ ID NO: 37, CDR2 being SEQ ID NO: 38, CDR3 being SEQ ID NO: 39; (n) CDR1 being SEQ ID NO: 40, CDR2 being SEQ ID NO: 41, CDR3 being SEQ ID NO: 42; (o) CDR1 being SEQ ID NO: 43, CDR2 being SEQ ID NO: 44, CDR3 being SEQ ID NO: 45; (p) CDR1 being SEQ ID NO: 46, CDR2 being SEQ ID NO: 47, CDR3 being SEQ ID NO: 48; (q) CDR1 being SEQ ID NO: 49, CDR2 being SEQ ID NO: 50, CDR3 being SEQ ID NO: 51; (r) CDR1 being SEQ ID NO: 52, CDR2 being SEQ ID NO: 53, CDR3 being SEQ ID NO: 54; (s) CDR1 being SEQ ID NO: 55, CDR2 being SEQ ID NO: 56, CDR3 being SEQ ID NO: 57; (t) CDR1 being SEQ ID NO: 58, CDR2 being SEQ ID NO: 59, CDR3 being SEQ ID NO: 60. (See FIG. 1B) All the above described sdAbs (a)-(t) bind to mouse TLT-1. sdAbs (a), (b), (c), (e), (f), (g), (i), (l), (m), and (s) also bind to human TLT-1.

In one embodiment, sdAbs are used to prepare HcAb. For example, the selected gene of sdAbs can be codon-optimized and fused to a human IgG1 Fc fragment using a polymerase chain reaction; then the entire HcAb gene fragment is subcloned into an expression vector for expression in CHO cells. The recombinant HcAbs can be purified by Protein A chromatography and the purity of the proteins confirmed with SDS-PAGE and SEC-HPLC.

In one embodiment, the anti-TLT-1 antibody in the conjugate or fusion protein of the present invention comprises sdAbs or HcAb having CDR1, CDR2, and CDR3 sequences as described above in (a)-(t).

In another embodiment, the anti-TLT-1 antibody in the conjugate or fusion protein of the present invention comprises sdAbs or HcAb having CDR1, CDR2, and CDR3 sequences as described above in FIG. 3B of US20220041716, in particular, sdAb 2-33 (shown as SEQ ID: 68 in the reference) and sdAb 2-132 (shown as SEQ ID: 76 in the reference).

In one embodiment, a chimeric or humanized heavy chain-only antibody can be prepared by fusing HcAb to human hinge, CH2 and CH3 immunoglobulin domains. The heavy chain-only antibody can be used as a fusion partner with a cytokine domain (e.g., IL-2 domain) or can be used for conjugating to an anti-neoplastic agent (e.g., MMAE).

The following examples further illustrate the present invention. These examples are intended merely to be illustrative of the present invention and are not to be construed as being limiting.

EXAMPLES

TABLE 1

| Abbreviations | |
| --- | --- |
| Abbreviation Name | Description |
| TLT-1 | TREM-like transcript-1 |
| sdAb | Single domain antibody |
| HcAb | Heavy chain-only antibody |

TABLE 1-continued

Abbreviations

| Abbreviation Name | Description |
|---|---|
| VHH | Variable domain of the heavy chain immunoglobulin |
| chHcAb | Chimeric and humanized heavy chain-only antibody |
| CHO | Chinese hamster ovary |
| BHK | Baby Hamster Kidney |
| HEK | Human embryonic kidney |
| SEQ | Sequence |
| CDR | Complementary determining regions |
| PBMC | Peripheral blood mononuclear cell |
| GLY | Glycine |
| SER | Serine |
| HIS | Histidine |

Example 1. Generation of Anti-Human TLT-1 Single Domain Antibodies (sdAbs) by Screening Naïve Llamas Library The llama naïve phage display library stock was precipitated with PEG/NaCl and re-suspended in PBS for panning. Solid panning strategies were performed to develop this project. For solid phase panning, the phage libraries were panned against mTLT1-Fc protein. The eight wells of microplate were coated with antigen at concentration 100 mM in PBS (phosphate-buffered saline), 125 ul/well, at 4° C. overnight, while non-specific binding wells were coated with casein. Llama naïve phage display library phage particles ($2\times10^{12}$ pfu/pool) were diluted in a blocking buffer. Then, the phage particles were transferred into negative protein (human Fc)-coated wells and incubated for 1 hour with shaking at RT. Subsequently, the phage particles were transferred into target antigen (mTLT-1) coated wells and incubated for 1 hour with shaking at RT. After incubation, unbound/nonspecifically bound phages were removed by decanting and washing with 0.05% PBST for ten times and 3-5 times with PBS. The bound phage (beads/well/cells) were eluted by TEA and neutralized with 1M Tris-HCl (pH7.4). The phage eluate was used to infect 10 ml exponentially growing *E. coli* TG1 at 37° C. Phage particles were prepared for subsequent rounds of biopanning, by amplification and rescue using M13K07 helper phage as per standard procedures. The former round amplified phage was used as the input phage for the next round biopanning. The output-infected glycerol bacteria were cultured to the logarithmic growth stage, and then M13K07 helper phage was added to amplify the phage overnight after infection. The next day, the phage was precipitated and the titer was counted for the next round. The 2nd and 3rd round of panning followed the same protocol as the 1st round of panning, with a lower concentration (40 mM) of mTLT1 protein to increase the panning pressure. In addition, 20 ug/ml of human Fc was added in the system for competition. After a third round of panning, the infected TG1 were plated on the LB-Amp+ plates at round 3 for screening. Single colonies were picked up and a binding activity was performed to both mTLT-1 and hTLT-1 and were validated by monoclonal phage ELISA.

Individual colonies were grown in 96-deep-well plate and rescued by M13KO7 helper phage at 30° C. overnight. In the meantime, 96-well ELISA microtiter plates were coated with 1 μg/ml of a target antigen (mouse TLT-1 or human TLT-1) in coating buffer overnight at 4° C. The plates were blocked with 5% MPBS. After rinsing, 50 μl of phage supernatant from each overnight cultured deep wells were added to the plates for 2 hours incubation at RT. After rinsing the plates three times with wash buffer, the HRP conjugated anti-M13 monoclonal antibody was added to the plates for 45 minutes at RT. The plates were washed for an additional six times and the substrate solution were added to the wells for developing the reaction. The absorption was measured at 450 nm using a spectrometer. The top 20 antigen binders to mouse and/or human TLT-1 with good signals (see Table 2) were sent for DNA sequencing using a standard procedure developed by GenScript (New Jersey, US).

The human Fc control groups presented an expected low signal, which indicated that all of the top 20 clones did not cross-react with the Fc tag and were bound to the target specifically (Table 2).

TABLE 2

The summary results of 20 unique clones

| Clone ID | mTLT-1 (OD) | hTLT-1 (OD) | h-Fc (OD) | Frequency |
|---|---|---|---|---|
| AHP11901 | 2.836 | 0.186 | 0.059 | 1 |
| AHP11903 | 2.787 | 2.391 | 0.054 | 1 |
| AHP11924 | 2.711 | 2.31 | 0.06 | 1 |
| AHP11939 | 2.763 | 0.068 | 0.065 | 1 |
| AHP11946 | 2.647 | 1.95 | 0.062 | 1 |
| AHP11983 | 3.365 | 2.772 | 0.234 | 15 |
| AHP11986 | 2.902 | 1.078 | 0.112 | 1 |
| AHP11989 | 0.95 | 0.095 | 0.232 | 2 |
| AHP11993 | 2.91 | 0.658 | 0.139 | 1 |
| AHP11995 | 3.161 | 0.092 | 0.171 | 2 |
| AHP11997 | 1.507 | 0.176 | 0.188 | 1 |
| AHP12001 | 3.169 | 2.141 | 0.154 | 7 |
| AHP12006 | 3.361 | 2.588 | 0.195 | 83 |
| AHP12018 | 1.364 | 0.148 | 0.294 | 11 |
| AHP12019 | 0.873 | 0.113 | 0.178 | 6 |
| AHP12022 | 0.588 | 0.175 | 0.191 | 2 |
| AHP12024 | 0.954 | 0.188 | 0.204 | 1 |
| AHP12026 | 0.716 | 0.133 | 0.137 | 1 |
| AHP12028 | 0.967 | 0.151 | 0.19 | 1 |
| AHP12034 | 0.853 | 0.163 | 0.252 | 1 |

Example 2. Tumor Cell Induced Platelet Activation

Blood was collected from healthy volunteers with citrate anticoagulant and centrifuged at 180 g for 10 minutes. The platelet-rich plasma was then collected, stored at 37° C. and used within two hours. To evaluate whether cancer cells can bind to and further activate the platelets, platelet-rich plasma was incubated with the cancer cell line MDA-MB-231, for 6 hours at 37° C. The cancer cell and platelet mixtures were then stained with an anti-CD42b-PE antibody (BD Biosciences, Franklin Lakes, NJ, United States), as a platelet marker; anti-CD62P-APC antibody, as an activated platelet marker, and anti-TLT-1 sdAb-FITC. To analyze the platelet binding to the cancer cells, the cancer cell population was gated, first based on the cell size, and the varying signal of platelet binding in the same gating area were analyzed by Flow cytometry. The results demonstrate that platelets can bind directly to cancer cells (FIG. 3A); all platelets (100%) associated with the cancer cells are activated (FIG. 3B), and anti-TLT-1 antibody can specifically bind to tumor activated platelets (FIG. 3C).

Example 3. Generation of TLT-1-HcAb ADC Molecule and Cathepsin B Digestion sdAbs are small in molecular weight (12-15 kDa) and directly conjugating small molecules of MMAE to it may cause conformational changes and alter their binding properties to a specific target. To avoid potential issues and to facilitate the conjugation of MMAE, a TLT-1 HcAb was produced. In brief, the selected gene of sdAbs were codon-optimized and fused to a human IgG1 Fc fragment using a polymerase chain reaction; then the entire HcAb gene fragment was subcloned into an expression vector for expression in CHO cells. The recombinant HcAbs were purified by Protein A chromatography and the purity of the proteins were confirmed with SDS-PAGE and SEC-HPLC.

Figure 3:
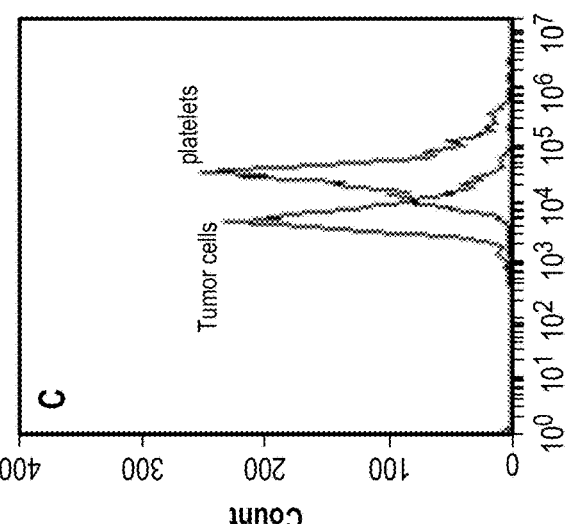
FIG. 3 shows that the tumor cells, represented by MDA-MB-231 (ATCC HTB-26), can bind and activate platelets, allowing the TLT-1 HcAb to recognize the TLT-1 receptor expressed on the surface of platelets. Human platelet-rich plasma was incubated with MDA-MB-231 cells and stained with a PE-conjugated anti-CD42b antibody, an APC-conjugated anti-CD62P and a FITC-conjugated anti-TLT-1 HcAb. The MDB-MB-231 cell region was gated for platelet/activated platelet analysis. (A) Analysis of the region of cancer cells positive for CD42b, confirming that platelets can bind
Figure 3:
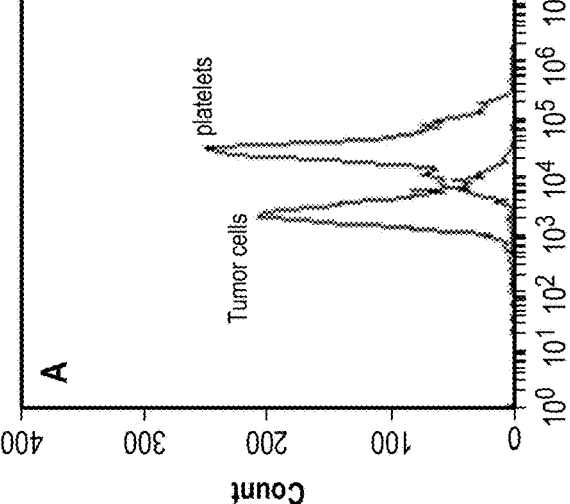

In this experiment, two anti-TLT sdAbs described in FIG. 3B of U.S. Publication No. US2022/0041716, i.e., 2-33 (SEQ 68) and 2-132 (SEQ 76) were used. In addition, an anti-GFP sdAb was used as a non-TLT targeting sdAb, which is a negative control in animal study (FIG. 6). The sdAbs of 2-33, 2-132, and GFP were used to prepare HcAbs (HX41, HX42, and HX06-8, respectively).

HcAbs (HX41, HX42 and HX06-8) were incubated with the reducing reagent, TCEP (Tris(2-carboxyethyl) phosphine), for 5 hours at 37° C. Then, 10 mg/ml of mc-vc-PAB-MMAE (Levena Biopharma, Suzhou, China) in 10% dimethylacetamide (DMA) was added to above solution for 1 hour at 4° C. The final products (HX41-MMAE and HX42-MMAE) were isolated through a 40 kDa desalting column and stored in 20 mM L-histidine (pH 5.5). The purified products were characterized with UV-VIS spectrometry for protein concentration, SEC-HPLC for purity and aggregation, HIC-HPLC and PLRP-HPLC for DAR analysis and distribution, C18-HPLC for free drug residue and Endosafe-PTS (Charles River Laboratories) for endotoxin level determination.

The linker used in generating TLT-1 HcAb-MMAE (ADC) is a Cathepsin B-cleavable linker, which is able to enable the activation of an inactive prodrug to an active cytotoxic form, due to the enriched localization of the enzyme in the tumor microenvironment. Prior to cytotoxicity studies, an in vitro assay was performed to demonstrate that the MMAE conjugated through the cleavable linker can be released in the presence of Cathepsin B. To the Britton-Robinson buffer (40 mM acetic acid, 40 mM phosphoric acid, and 40 mM boric acid, pH 4.5), 1 mM EDTA, 10 mM cysteine, pH 4.5, Cathepsin B and DMA, samples of HX41-MMAE and HX42-MMAE antibodies, as well as the linker, mc-vc-PAB-MMAE, were added. IgG1-MMAE was added as well as a control. For negative controls, samples without Cathepsin B were prepared under the same reaction conditions. All reactions were incubated at 22° C. for 15 min and then 37° C. for 17 hours. The efficiency of the Cathepsin B digestion was analyzed with LC-MS, and the results indicated that HX-41/42-MMAE and HX06-8-MMAE were completely digested (data not shown).

Example 4. In Vitro Cytotoxicity Assay of HX41-MMAE and HX42-MMAE

HX41-MMAE, HX42-MMAE and HX06-8-MMAE-mediated cytotoxicity of MDA-MB-231-luc cells was determined by cell viability measurements. MDA-MB-231-luc cells (cells in which the breast adenocarcinoma cells are transfected with a luciferase gene) were plated at 4000 cells/well into 96-well clear bottom black plates in 80 µl RPMI 1640 medium containing 10% FBS and incubated at 37° C., 5% $CO_2$. HX41-MMAE and HX42-MMAE antibodies (with/without Cathepsin B cleavage) were serially diluted separately and incubated with MDA-MB-231-luc cells for 96 hours. Cell viability was then measured using CELLTITER-GLO® (luminescent cell viability assay, Promega, #G7573) as instructed by the manufacturer. IgG1-

MMAE was used as the positive control. The cytotoxicity effect obtained with HX41-MMAE, HX42-MMAE and IgG1-MMAE were calculated by comparing the luminescence values obtained with 'cells only' control wells with the following equation: Cytotoxicity $\%=100* (V_{cell\ only}-V_{sample})/V_{cell}$ only. Four-parameter non-linear regression analysis was used to obtain $IC_{50}$ values for cytotoxicity using GRAPHPAD PRISM® (Computer software for analyzing and graph scientific data) six software.

As shown in FIG. 4, cytotoxicity effects were observed with all samples in the presence of Cathepsin B. The results confirmed that MMAE could be released by Cathepsin B-enriched. The cytotoxicity effects of HX41-MMAE, HX42-MMAE, and HX06-8-MMAE were confirmed with equal dose-dependent killing of the triple-negative breast adenocarcinoma cell line MDA-MB-231 and similar IC50.

Example 5. Antitumor Effect of TLT-HcAb-MMAE Molecules

To investigate the antitumor therapeutic effect of TLT-1 HcAb-MMAE, a triple-negative breast cancer cell line in vivo, MDA-MB-231 (ATCC HTB-26), were used in generating a mouse tumor model. In brief, the MDA-MB-231-luc tumor cells were suspended in 0.1 ml Dulbecco's PBS and implanted into the 4th left mammary fat pad of anesthetized female animals, followed by bioluminescent imaging of the luciferase genes (IVIS Spectrum In Vivo Imaging, Perkin Elmer) to confirm the inoculation. When the imaging signal reached to about $1.5×10^7$ pixel/sec/$cm^2$, the tumor size was considered significantly large enough to start the efficacy studies of HX41-MMAE and HX42-MMAE. PBS buffer was used as the negative control. Each group of animals consisted of eight mice and a total of six doses were administered intravenously (i.v.) at 6 mg/kg for each mouse every 4 days. The results indicated that on day 31 of the experiment, there was an 80% reduction in tumor volume as compared to mice treated with PBS. The treatments did not cause any visible side-effects as the mice were healthy during the experiment with no loss of body weight (FIG. 5). The results demonstrate that TLT-1-ADC constructs targeted to platelets is a new therapeutic target for tumor treatment.

Example 6. TLT-1 sdAb-IL2-His In Vitro Activity Calibration

The selected gene of TLT-1 sdAbs (sdAb 2-132) were codon-optimized and fused to human IL-2 gene fragment using a polymerase chain reaction at the C-terminus of a sdAb. A hexahistidine (6×His) sequence was attached to the C-terminus of each sdAb-IL2 fusion to facilitate protein purification. The entire sdAb-IL2-His gene fragment was subcloned into an expression vector for protein production in CHO cells. The recombinant sdAb-IL2-His was purified by metal chromatography and the purity of the proteins was confirmed with SDS-PAGE and SEC-HPLC. A GFP sdAb-IL2-His fusion protein was expressed and purified using the same method as negative control.

The biological activities of TLT-1-sdAb-IL2-His and GFP-sdAb-His fusion proteins, as well as of IL-2, were determined using CELLTITER-GLO® Luminescent Cell Viability Assay (Promega) using CTLL-2 cells (ATCC TIB-214, a clone of cytotoxic T-cells derived from a C57BL/6 mouse that are IL-2-dependent for growth). Briefly, 10×106 cultured CTLL-2 cells were starved in CTLL-2 culture medium RPMI 1640 (Gibco) supplemented with 10% FBS, 1% Ultra-glutamine, 25 mM Hepes (Gibco), 0.05 mM B-mercaptoethanol (Sigma Aldrich) and without IL-2 for 24 hours. Starved CTLL-2 cells (2×104 cells/well) were seeded in 96-well plates in CTLL-2 culture medium containing varying concentrations (10-12-10-9 M) of IL-2, TLT-1-sdAb-IL2-His and GFP-sdAb-IL2 fusion proteins; assays were performed in triplicate. After 24 hours at 37° C., cell proliferation was determined by luminometry. The results indicated that all TLT-1-sdAb-IL2-His fusion proteins retained the same in vitro activity as commercial human recombinant IL-2 in this proliferation assay.

Example 7. Antitumor Effect of TLT-1 sdAb-IL2 Fusion

To investigate the antitumor therapeutic effect of TLT-1 sdAb-IL2 fusion, two mouse syngeneic tumor models, MC38/C57 (colorectal tumor) and 4T1/Balb/c (breast tumor), were used in the study. For each animal model, 7 animals/group were treated with three testing compounds at various concentrations, with PBS as a control; when the tumor size reached 30-40 mm 3 post-tumor cell inoculation, the effect of treatment on tumor growth and body weight was assessed by measuring the tumor. A significant reduction in tumor size could be observed in the MC38 mouse model at day 12 (FIG. 6A) compared to non-targeted (GFP sdAb-IL2 fusion) and vehicle (PBS) controls. In the 4T1 model, the targeted treatment by TLT-1-sdAb IL2 fusion also generated remarkable reduction in tumor size compared to controls (FIG. 6B). These results, in two different syngeneic tumor models, confirmed that by targeting the TLT-1 receptor expressed on the surface of activated platelet, the tumor growth can be inhibited effectively. As a consequence, these molecules can be used as specific applications that can be used across a broad range of tumor cell types.

Example 8. Tumor Section Immune-Staining with TLT-1 sdAb-Fc Fusions

MDA-MB-231 4T1 tumor tissues were taken from mice at the end of the experiments described in Examples 5 and 6, respectively. They were formalin-fixed (24-72 hours) and paraffin-embedded. Three-um-thick sections were mounted onto (SUPERFROST® microscope slide) Plus-coated slides (Menzel, Braunschweig, Germany) and dried for 60 minutes at 68° C. and further baked for 2 hours. Sections were de-waxed in Xylene I/II and rehydrated through a graded series of ethanol and rinsed in water. Endogenous peroxidase activity was blocked with 3% hydrogen peroxidase for 25 minutes. Heat-induced antigen retrieval was performed in a microwave oven in 10 mM Tris/EGTA (pH 9.0). Sections were cooled for 15 minutes at room temperature and rinsed in Tris-buffered saline (TBS) for 15 minutes. Sections were treated with 3% BSA in TBS for 30 minutes to block non-specific binding sites.

Anti-TLT-1 antibody (AHP11983) was initially tested with different pre-treatments and dilutions to optimize the final staining protocol used in the study. Tissue sections were then incubated with a primary antibody overnight at 4° C. and washed three times on the following day at room temperature. Detection was performed by incubating HRP-coupled goat anti-human Fc antibody with washed tumor sections for 50 minutes at room temperature followed by visualization with diaminobenzidine (DAB) chromogen. Non-platelet binding HcAb (HX06-8), HRP goat anti-human Fc antibody and/or DAB chromogen were included as negative controls. All sections were rinsed in water and then counterstained with hematoxylin, and then dehydrated for storage.

Immunostained sections were digitized using a NANO-ZOOMER® (digital slide scanner, Hamamatsu Photonics, Japan) automated slide scanner with a 400X objective (FIGS. 7A and 8A). Software (Image Pro Plus) from SAA Inc (China) was used to attain a quantitative estimate of all analyzed factors. Image analysis protocols were developed by training the software to recognize specific colors of the stained activated platelet. The results of image analyses of all sections were reviewed by the observer to exclude errors The results indicated that tumor cell-activated platelets were specifically recognized with anti-TLT-1 antibody AHP11983 in both tumor cell types, namely, MDA-MB-231 and 4T1. With a negative control anti-GFP antibody (NX06-8), secondary HRP goat anti-human Fc antibody or DAB only, no tumor-associated platelet staining was observed. The DAB intensity (FIGS. 7B and 8B) of each tumor section was measured by using immunohistochemistry image scanning software (Image Pro Plus 6).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A conjugate or a fusion protein comprising: (a) an anti-TLT-1 (triggering receptors expressed on myeloid cells like transcript-1) antibody, and (b) a payload, wherein the anti-TLT-1 antibody and the payload are covalently linked together, and the payload is an anti-neoplastic molecule or an anti-mitotic molecule, wherein the anti-TLT-1 antibody comprises a variable domain of heavy chain antibody (VHH) comprising heavy chain complementary determining region (HCDR) 1 having the amino acid sequence of SEQ ID NO: 16, HCDR2 having the amino acid sequence of SEQ ID NO: 17, and HCDR3 having the amino acid sequence of SEQ ID NO: 18.

2. The conjugate of claim 1, wherein the anti-neoplastic molecule is Dxd, PBD (pyrrobenzodiazepine) and IBD (indolinobenzodiazepine).

3. The conjugate of claim 1, wherein the anti-mitotic molecule is MMAE (monomethyl auristatin E); MMAF (monomethyl auristatin F); dolastatin 10, DM1 (N(2')-deacetyl-N(2)-(3-mercapto-1-oxopropyl)-maytansine), or DM4.

4. The conjugate of claim 1, further comprising a linker between (a) and (b).

5. The conjugate of claim 4, wherein the linker comprises a protease cleavage site, wherein the protease is tumor-expressed.

6. The conjugate of claim 5, wherein the protease is Cathepsin B, matrix metalloproteinase-2, matrix metallo-proteinase-9, legumain, dipeptidyl protease 4, prostate-specific antigen, renin, napsin A, or Granzyme B.

7. A method for treating cancer, comprising:
administering the conjugate or the fusion protein of claim 1 to a subject in need thereof,
binding the conjugate to TLT-1 expressed on the surface of activated platelets in tumor microenvironments,
delivering the payload to a tumor cell, and
killing the tumor cell.

* * * * *